Figure 1A:
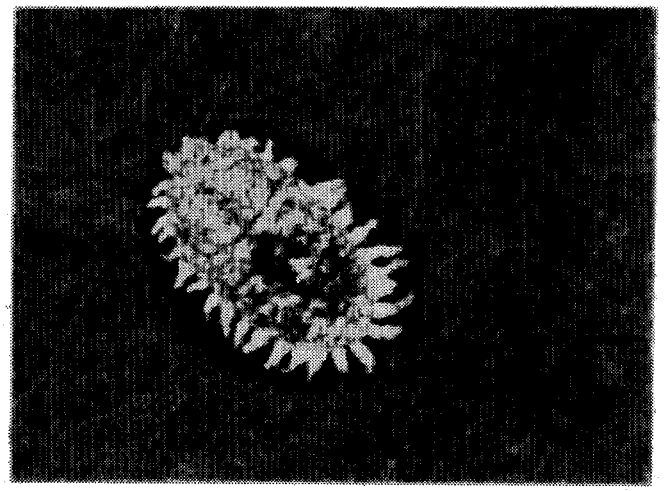
Figure 1B:
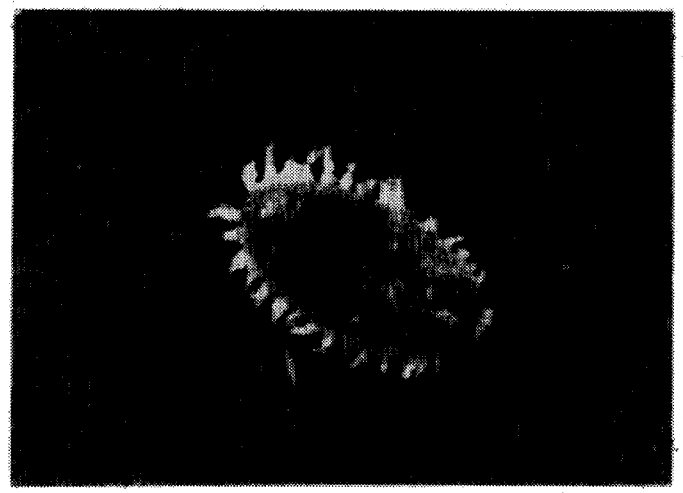
Figure 1C:
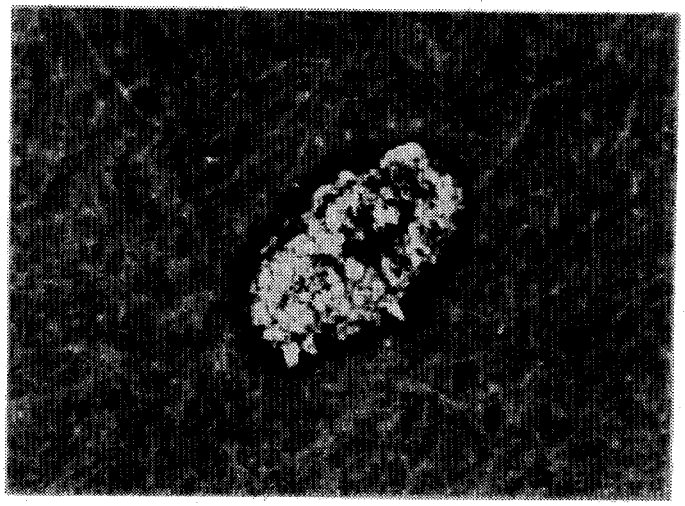
Figure 1D:
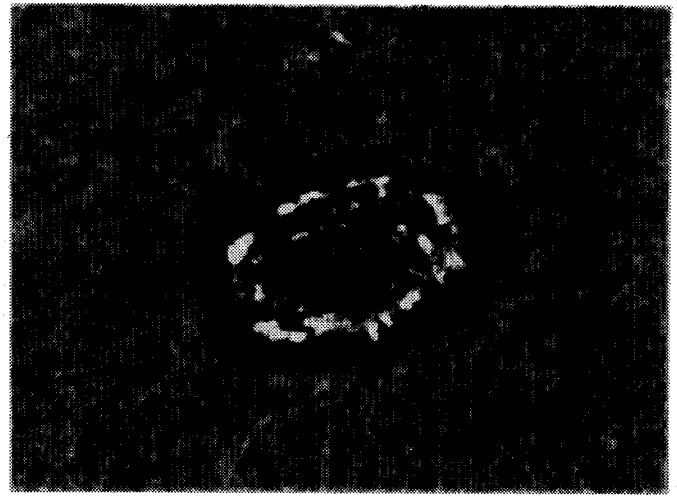
Figure 1E:
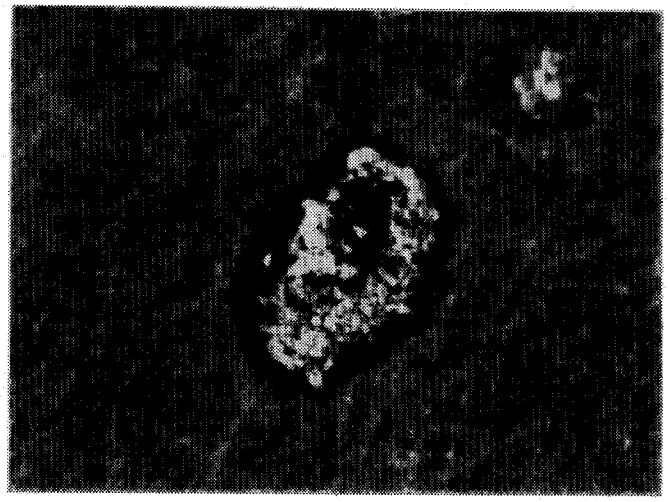
Figure 1F:
Figure 1G:
Figure 1H:

United States Patent [19]

Dezur et al.

[11] Patent Number: 5,614,203

[45] Date of Patent: Mar. 25, 1997

[54] ENVIRONMENTALLY SAFE PESTICIDE AND PLANT GROWTH ACCELERATOR

[75] Inventors: Terry M. Dezur, Santa Ynez; Richard W. Pollard, Solvang, both of Calif.

[73] Assignee: Environmentally Safe Systems, Inc., Solvang, Calif.

[21] Appl. No.: 380,101

[22] Filed: Jan. 30, 1995

[51] Int. Cl.$^6$ ................................................ A01N 25/04
[52] U.S. Cl. ................................................ 424/405; 424/45
[58] Field of Search ............................ 424/405, 45, 84

[56] References Cited

U.S. PATENT DOCUMENTS

| | | | |
|---|---|---|---|
| 2,578,652 | 12/1951 | Cassaday | 260/461 |
| 2,754,243 | 7/1956 | Gysin et al. | 167/33 |
| 2,962,521 | 11/1960 | Usui | 260/461 |
| 3,689,245 | 9/1972 | Weidman et al. | 424/405 |
| 3,719,467 | 3/1973 | Loux | 71/106 |
| 3,845,172 | 10/1974 | Magee | 260/956 |
| 4,065,558 | 12/1977 | Gordon | 424/216 |
| 4,321,258 | 3/1982 | Dunlap | 424/84 |
| 4,361,554 | 11/1982 | Saunders | 424/180 |
| 4,602,004 | 7/1986 | Cohen | 514/23 |
| 4,721,727 | 1/1988 | Mikolajczak et al. | 514/473 |
| 4,774,234 | 9/1988 | Puritch et al. | 514/86 |
| 4,891,222 | 1/1990 | Eichhoefer | 424/196.1 |
| 4,904,645 | 2/1990 | Puritch et al. | 514/65 |
| 4,946,700 | 8/1990 | Taguchi et al. | 426/520 |
| 4,983,591 | 1/1991 | Puritch et al. | 514/65 |
| 4,988,516 | 1/1991 | Herring | 424/659 |
| 5,009,710 | 4/1991 | Bewsey | 106/208 |
| 5,047,424 | 9/1991 | Puritch et al. | 514/521 |
| 5,078,782 | 1/1992 | Nielsen et al. | 71/100 |
| 5,089,266 | 2/1992 | Lee | 424/407 |
| 5,093,124 | 3/1992 | Kulenkampff | 424/406 |
| 5,110,804 | 5/1992 | Lee | 514/60 |
| 5,118,506 | 6/1992 | Eichhoefer | 424/196.1 |
| 5,120,542 | 6/1992 | Scher et al. | 424/405 |
| 5,125,967 | 6/1992 | Morpeth et al. | 106/18.22 |
| 5,174,998 | 12/1992 | Ijitsu et al. | 424/410 |
| 5,198,467 | 3/1993 | Milks | 514/553 |
| 5,317,042 | 5/1994 | Narayanan | 514/772 |
| 5,342,630 | 8/1994 | Jones | 424/717 |
| 5,405,612 | 4/1995 | Locke et al. | 424/410 |

OTHER PUBLICATIONS

International Searching Authority, "Notification of Transmittal of the International Search Report or the Declaration", 7 Jun. 1996, Form PCT/ISA/220, 3 pages.

Ernest W. Flick, "Advanced Cleaning Product Formulations", vol. 2, Noyes Publications, 1994, pp. 96 and 98.

*Primary Examiner*—Thurman K. Page
*Assistant Examiner*—Sharon Howard
*Attorney, Agent, or Firm*—Webb Ziesenheim Bruening Logsdon Orkin & Hanson, P.C.

[57] ABSTRACT

A substantially, environmentally safe pesticide comprising between about 3 and about 10% by weight of a surfactant, between about 1 and about 5% by weight of an alkali metal silicate and between about 5 and about 25% by weight of a mineral oil and the balance being water. The pesticide can also include between about 0 and about 30% by weight of one or more additional substances, wherein the none of the one or more additional substances is itself a pesticide. Preferably, the one or more substances is between about 1 and about 10% by weight of plant extract and about 0.2 and about 5% by weight of fish extract or a combination of both. The plant extract and fish extract function to negate the phytotoxicity of the other substances and to accelerate plant growth. The remainder of the pesticide is substantially water.

21 Claims, 4 Drawing Sheets
(4 of 4 Drawing(s) in Color)

ENVIRONMENTALLY SAFE PESTICIDE AND PLANT GROWTH ACCELERATOR

BACKGROUND

This invention relates to pesticides that are substantially environmentally safe and are substantially non-toxic to large animals.

Yields in agriculture and in horticulture are limited by a number of agents and conditions. Among the agents and conditions affecting plant yields are insects, fungi and suboptimal soil.

A wide variety of man-made compositions have been used in agriculture and horticulture to control damaging insects and fungi. Further, a number of compositions have been used to improve suboptimal soil conditions, thereby accelerating plant growth.

Previously known pesticides have had a variety of problems. Many of these compositions are toxic to large animals, including man, in addition to being toxic to insects or fungi. Further, many compositions that function as pesticides accumulate in the environment to levels considered to be unsafe. In addition, many of these compositions have been found to contaminate natural sources of drinking water.

Such problems have lead the government to ban the use of many pesticides, including DDT, Chlorodane, Lindane, Aldrin, Heptachlor, Dieldrin and Mirex. Other compositions, though still in use, present varying degrees of unwanted toxicity.

Besides unwanted toxicity, presently known pesticides have other problems. They tend to be complex and expensive to produce, and many have disadvantageous storage requirements. Further, it is generally necessary to apply multiple pesticides to obtain satisfactory control of a variety of pests. This is necessary to avoid the labor costs of applying several individual pesticides in several separate applications, one at a time.

Therefore, it would be advantageous to have a single composition with activity against a broad range of pests but which is substantially non-toxic to large animals and which is environmentally safe. Further, it would be advantageous for the composition to also function as a plant growth accelerator. Ideally, such a composition would be easy and inexpensive to produce and to use.

SUMMARY

The present invention is directed to a pesticide that satisfies these needs. The pesticide comprises between about 3 and about 10% by weight of a surfactant, preferably a nonionic surfactant, between about 1 and about 5% by weight of an alkali metal silicate, preferably sodium metasilicate, and between about 5 and about 25% by weight of a mineral oil, preferably a light mineral oil. It optionally comprises between about 0 and about 30% by weight of one or more additional substances, wherein none of the one or more additional substances is itself a pesticide. The balance of the pesticide is water.

Preferentially, the one or more additional substances include a plant growth accelerator such as between about 1 and about 10% by weight of plant extract, between about 0.2 and about 5% by weight of a fish extract and a combination of both.

The pesticide of the present invention can be diluted with water in a water to pesticide ratio between about 0:1 and about 50:1 and more preferably in a water to pesticide ratio between about 2:1 and about 10:1.

The present invention is also directed towards a method for controlling pests, comprising applying an effective amount of the pesticide according to the present invention to pests or to a surface, plant or soil containing or potentially containing pests.

FIGURES

The file of this patent contains at least one color photograph. Copies of this patent with color photographs will be provided by the Patent and Trademark office upon request and payment of the necessary fee.

The features, aspects, and advantages of the present invention will become better understood with regard to the following description, appended claims, and accompanying photographs where:

Photographs 1A and 1B show a top and bottom view, respectively, at approximately 20× to 25× magnification of a mealybug before application of the pesticide according to the present invention;

Photographs 1C and 1D show a top and bottom view, respectively, at approximately 20× to 25× magnification of the mealybug in photographs 1A and 1B 10 minutes after application of the pesticide according to the present invention;

Photographs 1E and 1F show a top and bottom view, respectively, at approximately 20× to 25× magnification of the mealybug in photographs 1A and 1B 20 minutes after application of the pesticide according to the present invention; and Photographs 1G and 1H show a top and bottom view, respectively, at approximately 20× to 25× magnification of the mealybug in photographs 1A and 1B 30 minutes after application of the pesticide according to the present invention.

DESCRIPTION

The present invention is a pesticide comprising several substances. Each substance, or a chemically-related substance, has been previously added to pesticidal compositions for various purposes, such as emulsifying agents, dispersing agents or carriers. It has also been known in the prior art to combine some of the several substances, or chemically-related substances, in a composition which includes at least one additional substance whose specific function was pesticidal. We discovered, however, that the several substances which comprise the present invention, when combined in certain relative ratios, synergistically functions as a potent pesticide themselves, without including a separate pesticidal substance. The result is that the several substances which comprise the present invention, advantageously form a pesticide that is easy and inexpensive to manufacture, easy to apply and environmentally safe. Further, in one embodiment, the invention advantageously functions as a plant growth accelerator in addition to being a pesticide.

As used herein "pesticide" means a composition which exhibits either insecticidal or fungicidal properties or both. As used herein, the term "insecticide" refers to a composition which substantially renders harmless or kills insects. As used herein "fungicide" refers to a composition which substantially renders harmless or kills fungi.

As used herein "insect" refers to animals of the phylum or related to the phylum Arthropoda. The term includes, but is not limited to, both soft-bodied and hard-bodied animals of the orders of Homoptera, Coleoptera, Lepidoptera, Diptera, Protura, Thysanoptera, Orthoptera, Isoptera, Dermaptera, Mallophaga, Anoplura, Hemiptera, and Hymenoptera.

As used herein, the term "fungi" refers to a group of organisms that includes molds, mushrooms and mildews. Examples include, but are not limited to, leaf spot, root rot, black spot, brown rot, Anthracnose, Botrytis, dampening off, downey mildew, powdery mildew, peach leaf curl, verticilium wilt, fusarium wilt rust, pithium and alterneria.

As used herein, the term "plant growth accelerator" refers to a substance that increases the rate of plant growth significantly above the rate without the substance.

According to one embodiment of the present invention there is provided a pesticide that comprises a small number of readily obtainable substances in volumetric or weight ratios within specific ranges. When combined, the substances act synergistically to produce a environmentally safe pesticide and, in one embodiment, a pesticide which also functions as a plant growth accelerator.

The pesticide according to the present invention comprises at least three substances; a surfactant, a silicate and a mineral oil. Additionally, the pesticide can include one or more substances where none of the one or more additional substances is itself a pesticide. The balance of the pesticide is water. Preferentially, the one or more substances are a plant extract, a fish extract or both.

Surfactants are a class of materials which are capable of reducing the surface tension of a liquid when present in relatively low concentrations. Surfactants may be ionic, anionic or nonionic. In the present invention, a nonionic surfactant is preferred. While a variety of nonionic surfactants are known to those with skill in the art, and are suitable for incorporation into the pesticide of the present invention, primary alcohol alkoxylate is particularly preferred. This surfactant, alkyloxypolyethyleneoxypolypropyleneoxy ethanol, goes under the trade name Triton™ XL-80N Surfactant and is available from Union Carbide Corp., Houston, Tex.

The pesticide of the present invention further includes an alkali metal silicate. Preferentially, it includes a sodium silicate. More preferentially, it includes sodium metasilicate, which has the formula $Na_2SiO_3$. Sodium metasilicate is preferred over other forms of sodium silicate because it tends not to absorb moisture from the atmosphere as readily as some forms of sodium silicate, such as sodium silicate pentahydrate. Also, sodium metasilicate does not naturally contain significant amounts of water. Therefore, it a particularly potent form (on a % by weight basis) of sodium silicate for combination with the other substances comprising the invention. Sodium metasilicate is available from a variety of sources known to those with skill in the art, including OxyChem®, of Niagara Falls, N.Y. When sodium metasilicate is used, the pH of the pesticide should be at least about 7.5 or greater, and preferably 8.5 or greater.

The pesticide of the present invention further includes a mineral oil. Preferentially, the mineral oil is a light mineral oil, such as a white mineral oil, N.F. Suitable light mineral oil is available from Penreco, Karns City, Pa. or Los Angeles, Calif., under the name Drakeol 7®.

Additionally, the pesticide can comprise one or more substances where none of the one or more substances is itself a pesticide. That is to say, the one or more substances, used alone in a significant concentration, do not exhibit substantial pesticidal properties. The one or more substances is preferentially a plant extract. A suitable plant extract is made from seaweed, such as hydrolyzed kelp. One source of suitable plant extract is the product Garden MaxiCrop, available from Maxicrop U.S.A., Inc. Other sources of suitable plant extract include Kelco Co., Los Angeles, Calif. and the product Acadian Seaplants Seaweed Extract™ available from Acadian Seaplants Ltd., Dartmouth, Nova Scotia, Canada.

The pesticide of the present invention can further include a fish extract. Preferably, the fish extract is a substantially water-soluble powder, or a liquid. One source of suitable fish extract is the product Neptunes "Supreme", available from Island Seed and Feed, Goleta, Calif.

The function of the plant extract and the fish extract is to act as a buffering agent to obviate or at least substantially lessen the phytotoxicity of the combination of the other substances in the pesticide according to the present invention. The nutritive qualities of the plant extract, particularly combined with the nutritive qualities of the hydrolyzed fish, further act to accelerate plant growth through foliar feeding.

The balance of the pesticide of the present invention is water. While the water may be from any of a variety of sources, including filtered or distilled water, ordinary drinking water is suitable.

According to one embodiment of the present invention, a pesticide is produced as follows. Approximately 303 g of Triton™ XL-80N Surfactant is added to approximately 3,790 g of water and mixed. Next, approximately 126 g of sodium metasilicate is added to the water/surfactant and mixed. Sufficient mixing time should be allowed to permit the sodium metasilicate to dissolve thoroughly. Then, approximately 755 g of light mineral oil is added and the components are mixed thoroughly while entraining as little air as possible.

The resultant composition is a potent pesticide. However, the solution is also phytotoxic to a variety of agriculturally or horticulturally desirable plant species. In order to negate the phytotoxic properties of this mixture, approximately 210 g of plant extract and 39 g of fish extract are added. Thus, the final composition of the pesticide is approximately 73% by weight of water, approximately 14.5% by weight of light mineral oil, approximately 5.8% by weight of Triton™ XL-80N Surfactant, approximately 4% by weight of plant extract, approximately 2.4% by weight of sodium metasilicate and approximately 0.75% by weight of fish extract.

When the pesticide of the present invention is used in a manner in which phytotoxicity is of concern, the plant extract and should be included. Additionally, fish extract is preferentially included.

Once the pesticide according to the present invention is produced, with or without the plant extract or fish extract, it can be diluted to a suitable strength for use, or alternately it can be produced using smaller quantities of substances other than water. For example, one-sixth the amount of substances other than water can be added to water to produce a pesticide.

The amount of dilution is based on the type of plant and type of pest upon which the pesticide is to be used. Some testing should be performed, therefore, in order to determine the appropriate amount of dilution.

A dilution can be produced by adding water in a water to pesticide ratio equal to about 0:1 to 50:1. More preferentially, the dilution is equal to about a ratio of water to pesticide of about 2:1 to 10:1.

The substances which form the pesticide of the present invention can be present in a range of relative ratios. Table I provides pre-dilution, preferred approximate ranges of substances by weight percent as well as the most preferred range. While preferred ranges are shown, other ranges are possible as would be appreciated by those with skill in the art.

TABLE I

PRE-DILUTION, PREFERRED RANGES IN PERCENT BY WEIGHT

| Substance | Preferred Range | Most Preferred Range |
|---|---|---|
| Water | 45–90 | 68–76 |
| Nonionic Surfactant | 3–10 | 5–7 |
| Silicate Powder | 1–5 | 2–3 |
| Mineral Oil | 5–25 | 13–16 |
| Plant Extract | 1–10 | 3–5 |
| Fish Extract | 0.2–5 | 0.2–2 |

When the pesticide of the present invention is used in a manner in which phytotoxicity is not a concern, the plant extract and fish extract can be omitted. When the pesticide of the present invention is used in a manner in which phytotoxicity is of concern, the plant extract should be included, and additionally, fish extract is preferably included. Both the plant extract and the fish extract function to negate phytotoxicity and improve the plant growth accelerator characteristics of the pesticide.

The pesticide of the present invention is preferentially applied at a certain dilution and a certain application rate. Application rate refers to the specific amount of pesticide applied per time.

The full strength solution is diluted, if necessary, according to the crop being treated and the pest for which control is desired. For example, the dilution for aphid control or spider mite control is one-half the dilution required for mealy bug control. A small scale trial application is preferred prior to large scale application to determine if any phytotoxic reaction is likely to occur. Any phytotoxic reaction which does become evident can be reduced by increasing the dilution.

The dilution is partially determined by the air temperature at the time of application. The higher the air temperature, the higher the dilution should be.

Both the dilution and the application rate are partially determined by the amount of new growth and maturity of the crop at the time of application. A lower dilution in early season, prior to tender new foliar growth emergence, can stop larval development of many pests, thereby eliminating the need for future applications as well as feeding and stimulating the target crop for greater resistance against insect infestation.

Maximum effectiveness is obtained when the pesticide is applied with sufficient time to dry on the application surfaces. For best results, it is preferred to thoroughly cover all foliar, and woody stems and branches, including soil surfaces. Further, early morning or late afternoon to evening are the preferred times for application.

Crops respond favorably and vigorously to a thorough soil spray or soil drench for purposes of fertilizing and growth stimulation. Further, they exhibit stress reduction due to drought and temperature extremes.

When used as a soil drench, a dilution of about 3–4 gallons to 100 gallons of water is preferred. The same dilution is preferred for dormancy spraying on woody ornamentals, dormant fruit and shade trees as well as a transplant assist or as a soil conditioner. A second application just prior to bud break in early spring is preferred as a dormant spray, particularly if rainy damp weather has occurred or is anticipated.

Protective clothing and gear should be worn according to governmental standards and regulations. The formula is environmentally safe and non-corrosive. Therefore, washing or rinsing application equipment and clothing with water is optional.

Examples of suitable application are as follows. For control of scale or mealybug at mid season, dilute about 4.5 oz of pesticide to 1 gallon of water, or about 3.5 gallons of pesticide to 100 gallons of water for a larger application, for an air temperature of less than about 75° F. For control of the same pests earlier in the season, at the time of tender new spring growth, a greater dilution of about 2.5 gallons of pesticide to 100 gallons of water is preferred. Then, preferably, a second application of the pesticide is applied within about 5 to 7 days. This second application is particularly preferred for control of some pests, such as whitefly, due to egg hatch on the target crop.

The pesticide is a penetrating contact spray. Application can be accomplished, for example, about once every five to seven days for serious infestations of pests. For less serious infestations of pests, the frequency of application can be reduced. Spraying the composition at regular intervals of about three to five weeks will maintain good pest control throughout the growing season. The composition can be used safely up through harvest time.

EXAMPLE 1

Acute Oral Toxicity Limit Test

The toxicity to large animals of the pesticide according to the present invention, occurring from a single orally administered dose, was evaluated as follows. Five male and five female young, healthy adult Wistar-derived albino rats, each weighing between about 200 and 300 grams were used for this evaluation. The animals were fed on water and Purina Rat Chow ad-libitum. The animals were fasted 18 to 24 hours prior to dosing but were allowed water ad-libitum. Feed was returned ad-libitum immediately after dosing.

A single oral dose of the pesticide according the present invention, and having a composition of approximately 73% by weight of water, approximately 14.5% by weight of light mineral oil, approximately 5.8% by weight of Triton™ XL-80N Surfactant, approximately 4% by weight of plant extract, approximately 2.4% by weight of sodium metasilicate and approximately 0.75% by weight of fish extract was delivered by gavage at a dose level of 5.0 g/kg body weight. The rats were individually caged and observed for mortality or signs of growth toxicity for fourteen days. At the end of the test period, all surviving animals were weighed and sacrificed, and necropsies were performed.

The results of this study are summarized in Table II. All test animals appeared healthy and exhibited weight gain throughout the observation period. Necropsies of the surviving test animals revealed that all organs were intact. No abnormalities or discolorations were noted.

TABLE II

| Animal # | Sex | Body Weight Initial (g) | Body Weight Final (g) | Dose Dosage (g) | Dose Delivered* (ml) | Mortality Day |
|---|---|---|---|---|---|---|
| 3009 | M | 236 | 251 | 1.18 | 1.20 | NA |
| 3011 | M | 240 | 261 | 1.20 | 1.22 | NA |
| 3020 | M | 235 | 242 | 1.18 | 1.20 | NA |
| 3021 | M | 238 | 255 | 1.19 | 1.21 | NA |

TABLE II-continued

| Animal # | Sex | Body Weight Initial (g) | Body Weight Final (g) | Dose Dosage (g) | Dose Delivered* (ml) | Mortality Day |
|---|---|---|---|---|---|---|
| 3026 | M | 236 | 248 | 1.18 | 1.20 | NA |
| x̄ | | 237 | 251 | 1.19 | 1.21 | |
| Range | | 190–284 | | | | |
| 3029 | F | 234 | 259 | 1.17 | 1.19 | NA |
| 3031 | F | 234 | 263 | 1.17 | 1.19 | NA |
| 3033 | F | 236 | 261 | 1.18 | 1.20 | NA |
| 3034 | F | 236 | 249 | 1.18 | 1.20 | NA |
| 3038 | F | 234 | 256 | 1.17 | 1.19 | NA |
| x̄ | | 235 | 258 | 1.17 | 1.19 | |
| Range | | 188–282 | | | | |

\* - 1 ml weighs 0.9777 g

EXAMPLE 2

Effectiveness Against Mealybugs

The insecticidal effectiveness of the composition according to the present invention, with respect to mealybugs, was evaluated as follows. Mealybugs are insects belonging to the Homoptera family. Other members of the Homoptera family include aphids, whiteflies and leafhoppers.

Mealybugs have elongate-oval bodies with well-developed legs. One type, Pseudococcidea, are covered with a waxy secretion that helps protect the bug from contact with pesticides.

Mealybugs receive their nutrition by sucking plant juices. Their bite into the plant frequently results in the introduction of fungal infections. The fungal infections cause significant damage to the plants in addition to the damage caused by the insect itself.

Photographs 1A through 1H illustrate the effect of a single application of the pesticide according to the present invention, and having a composition of approximately 73% by weight of water, approximately 14.5% by weight of light mineral oil, approximately 5.8% by weight of Triton™ XL-80N Surfactant, approximately 4% by weight of plant extract, approximately 2.4% by weight of sodium metasilicate and approximately 0.75% by weight of fish extract. All photographs were taken at approximately 20× to 25× magnification. Photographs 1A and 1B show a top view and bottom view of an untreated mealybug, respectively. The legs of the untreated bug exhibited substantial movement. A single application of diluted pesticide (about 4.5 oz to 1 gallon of water) according to the present invention was sprayed directly onto the insect to wet the insect thoroughly. The insect was then allowed to soak for a period of approximately 2 minutes before being removed and placed under the photo microscope.

Photographs 1C and 1D illustrate a top and bottom view, respectively, of the mealybug ten minutes after application. During the first ten minutes after application, the insect exhibited a spreading paralysis of its leg segments beginning proximally and extending distally.

Photographs 1E and 1F, and 1G and 1H, illustrate the top and bottom views of the bug twenty minutes after application and thirty minutes after application, respectively. As can be seen, the insect's protective waxy coating substantially dissolved. Further, the body of the insect became bloated and discolored, and the insect died.

EXAMPLE 3

Effectiveness Against Grape Phylloxera

The pesticidal effectiveness of the composition according to the present invention was further tested with respect to the different life stages of grape phylloxera in the three experiments below. Phylloxera is a form of aphid belonging to the Homoptera family. It lives primarily underground and attacks the roots of grapevines. After attaching to the roots, the insect feeds on the juices of the plants. The root produces a gall at the point of phylloxera attachment, which is evidence of the introduction of foreign material into the root. Fungal invasion into the plant through the point of attachment is common. Phylloxera is highly prolific, potentially producing billions of offspring in a single season, and causes extensive monetary loss to grape producers.

A. Assay of Effectiveness Against Phylloxera Eggs

The effectiveness of the pesticide according to the present invention was assayed against grape phylloxera eggs. Eggs used in these assays were one to three days old. The eggs were replicated into sets of 70 on 9 cm diameter filter paper discs which were previously moistened with 0.5 ml of distilled water in plastic petri dishes. The pesticide, according to one embodiment of the present invention, used in this assay had a composition of approximately 73% by weight of water, approximately 14.5% by weight of light mineral oil, approximately 5.8% by weight of Triton™ XL-80N Surfactant, approximately 4% by weight of plant extract, approximately 2.4% by weight of sodium metasilicate and approximately 0.75% by weight of fish extract. A control using distilled water was included in these assays.

The filter paper containing the eggs was moistened with 1 ml of distilled water or 1 ml of pesticide. Three replicates were used for each assay. The petri dishes were sealed with parafilm and then placed in plastic bags and in a plastic box in a growth chamber. The chamber was maintained at 24° C.

Egg mortality was determined after seven days. Egg hatching was considered the end point of the assay. An egg was considered to have succumbed to the treatment if it was dead or if the newly-hatched insect (crawler) died before emerging from the chorion completely. Hatched eggs were considered to have survived the treatment if the crawler succumbed to the pesticide on the filter paper soon after emergence. The results of this study are summarized in Table III.

TABLE III

| Treatment | Dead | Live | Total | % Mortality |
|---|---|---|---|---|
| Distilled water | 0 | 70 | 70 | 0 |
| | 1 | 69 | 70 | 1.4 |
| | 0 | 70 | 70 | 0 |
| Pesticide | 70 | 0 | 70 | 100 |
| | 70 | 0 | 70 | 100 |
| | 70 | 0 | 70 | 100 |

B. Assay of Effectiveness Against Nymph and Adult Phylloxera

The effectiveness of the pesticide, according to the present invention, was tested to determine its effectiveness against nymph and adult stages of phylloxera. Sections of Cabernet Sauvignon root pieces, each 4 cm long by 2–4 mm in diameter, were infected with 20–30 phylloxera eggs per root piece in petri dish chamber. After three weeks, small, medium and large nymphs, and adults were counted on each root pieces. Root pieces with insects were dipped in distilled water or the pesticide having a composition of approximately 73% by weight of water, approximately 14.5% by weight of light mineral oil, approximately 5.8% by weight of Triton™ XL-80N Surfactant, approximately 4% by weight of plant extract, approximately 2.4% by weight of sodium metasilicate and approximately 0.75% by weight of fish extract for ten seconds. The root pieces were then allowed to air dry.

The treated roots were placed on filter paper in petri dishes. The dishes were then sealed with parafilm, and placed in plastic bags in a plastic box in a growth chamber. The growth chambers were maintained at 24° C.

Four root pieces were used for each assay. Surviving animals were counted after one week. The results of this study are summarized in Table IV.

TABLE IV

| Treatment | Dead | Live | Total | % Mortality |
| --- | --- | --- | --- | --- |
| Distilled water | 2 | 17 | 19 | 10.5 |
| | 1 | 14 | 15 | 6.7 |
| | 5 | 16 | 21 | 23.8 |
| | 1 | 15 | 16 | 6.3 |
| Pesticide | 15 | 0 | 15 | 100 |
| | 19 | 0 | 19 | 100 |
| | 15 | 0 | 15 | 100 |
| | 16 | 0 | 16 | 100 |

C. Assay of Effectiveness Against Phylloxera Instar Establishment

The pesticide according to the present invention was further tested to determine its effectiveness in preventing first instar (crawler) establishment. Cabernet Sauvignon root pieces were dipped in distilled water or in pesticide having a composition of approximately 73% by weight of water, approximately 14.5% by weight of light mineral oil, approximately 5.8% by weight of Triton™ XL-80N Surfactant, approximately 4% by weight of plant extract, approximately 2.4% by weight of sodium metasilicate and approximately 0.75% by weight of fish extract. The root pieces were then allowed to air dry.

Treated root pieces were placed on a filter paper in plastic petri dishes. Twenty eggs were placed on each root. The dishes were sealed in parafilm, then placed in plastic bags in a plastic box in a growth chamber. The growth chambers were maintained at 24° C.

Four root pieces were used for each assay. After two weeks, the root pieces were examined and numbers of survivors which survived and succeeded to feed were counted. The results of this study are summarized in Table V.

TABLE V

| Treatment | Dead | Live | Total | % Mortality |
| --- | --- | --- | --- | --- |
| Distilled water | 6 | 14 | 20 | 30 |
| | 4 | 16 | 20 | 20 |
| | 8 | 12 | 20 | 40 |
| | 4 | 16 | 20 | 20 |
| Pesticide | 20 | 0 | 20 | 100 |
| | 20 | 0 | 20 | 100 |
| | 20 | 0 | 20 | 100 |
| | 20 | 0 | 20 | 100 |

Although the present invention has been described in considerable detail with reference to certain preferred embodiments thereof, other embodiments are possible. For example, the one or more additional substances can include substances that impart other desirable non-pesticidal properties, such as color or smell. Therefore, the spirit and scope of the appended claims should not be limited to the description of the preferred embodiments contained herein.

We claim:

1. A pesticide comprising:
    (a) between about 3 and about 10% by weight of a surfactant,
    (b) between about 1 and about 5% by weight of an alkali metal silicate,
    (c) between about 5 and about 25% by weight of a mineral oil,
    (d) between about 0.2 and about 30% by weight of one or more additional substances, wherein none of the one or more additional substances is itself a pesticide, and
    (e) the balance being water.

2. The pesticide of claim 1, comprising between about 5 and about 7% by weight of surfactant, between about 2 and about 3% by weight of alkali metal silicate, and between about 13 and about 16% by weight of mineral oil.

3. The pesticide of claim 1, wherein the surfactant is a non-ionic surfactant.

4. A dilution of the pesticide of claim 1, comprising the pesticide of claim 1 and up to 50 parts additional water.

5. The pesticide of claim 1, wherein the alkali metal silicate is a sodium silicate.

6. The pesticide of claim 1, wherein the mineral oil is a light mineral oil.

7. The pesticide of claim 1, wherein the one or more additional substances is selected from the group consisting of between about 1 and about 10% by weight of a plant extract, between about 0.2 and about 5% by weight of a fish extract and a combination of the foregoing.

8. The pesticide of claim 1, wherein the additional substance is seaweed extract or is hydrolyzed kelp extract.

9. A method for controlling pests, comprising the step of applying an effective amount of the pesticide according to claim 1 to pests or to a surface, plant or soil containing or potentially containing pests.

10. The method of claim 9, further comprising a step selected from the group consisting of repeating the application step at regular intervals of about once every five to seven days to control infestations of the pests, the step of repeating the application step at regular intervals of about three to five weeks to maintain control of the pests throughout a growing season, and a combination of the foregoing steps.

11. A pesticide consisting essentially of:
    (a) between about 3 and about 10% by weight of a surfactant,
    (b) between about 1 and about 5% by weight of an alkali metal silicate,
    (c) between about 5 and about 25% by weight of a mineral oil,
    (d) between about 0.2 and about 30% by weight of one or more additional substances, wherein none of the one or more additional substances is itself a pesticide, and
    (e) the balance being water.

12. The pesticide of claim 11, comprising between about 5 and about 7% by weight of surfactant, between about 2 and about 3% by weight of alkali metal silicate, and between about 13 and about 16% by weight of mineral oil.

13. A dilution of the pesticide of claim 11, consisting essentially of the pesticide of claim 11 and up to 50 parts additional water.

14. The pesticide of claim 11, wherein the surfactant is a non-ionic surfactant.

15. The pesticide of claim 11, wherein the alkali metal silicate is a sodium silicate.

16. The pesticide of claim 11, wherein the mineral oil is a light mineral oil.

17. The pesticide of claim 11, wherein the one or more additional substances is selected from the group consisting of between about 1 and about 10% by weight of a plant extract, between about 0.2 and about 5% by weight of a fish extract and a combination of the foregoing.

18. The pesticide of claim 11, wherein the additional substance is seaweed extract or is hydrolyzed kelp extract.

19. A method for controlling pests, comprising the step of applying an effective amount of the pesticide according to claim 11 to pests or to a surface, plant or soil containing or potentially containing pests.

20. The method of claim 19, further comprising a step selected from the group consisting of repeating the application step at regular intervals of about once every five to seven days to control infestations of the pests, the step of repeating the application step at regular intervals of about three to five weeks to maintain control of the pests throughout a growing season, and a combination of the foregoing steps.

21. A pesticide consisting essentially of:
  (a) between about 3 and about 10% by weight of a surfactant;
  (b) between about 1 and about 5% by weight of an alkali metal silicate;
  (c) between about 5 and about 25% by weight of a mineral oil; and
  (d) the balance being water.

* * * * *

UNITED STATES PATENT AND TRADEMARK OFFICE
CERTIFICATE OF CORRECTION

PATENT NO. : 5,614,203
DATED : March 25, 1997
INVENTOR(S) : Terry M. Dezur and Richard W. Pollard It is certified that error appears in the above-indentified patent and that said Letters Patent is hereby corrected as shown below:

Title Page, insert --Related U.S. Application Data, [63] Continuation-in-part of Ser. No. 372,288, Jan. 13, 1995, abandoned.--.

Column 1 Line 3, before BACKGROUND, insert --This application is a CIP of Ser. No. 08/372,288 abandoned Nov. 18, 1996.--.

Signed and Sealed this

Eleventh Day of November, 1997

Attest:

BRUCE LEHMAN

*Attesting Officer*  Commissioner of Patents and Trademarks